United States Patent [19]

Losev et al.

[11] Patent Number: 4,890,477

[45] Date of Patent: Jan. 2, 1990

[54] DEVICE FOR TESTING SKI SLIDING SURFACE

[76] Inventors: German P. Losev, ulitsa Tsvillinga, 42, kv.16.; Vasily A. Kamenskikh, ulitsa Belorechenskaya, 7, kv.16.; Pavel M. Vaisberg, ulitsa Bardina, 49, kv.40.; Boris N. Kharin, prospekt Lenina, 48, kv.95., all of Sverdlovsk, U.S.S.R.

[21] Appl. No.: 265,805

[22] PCT Filed: Jan. 15, 1987

[86] PCT No.: PCT/SU87/00003
§ 371 Date: Aug. 18, 1988
§ 102(e) Date: Aug. 18, 1988

[87] PCT Pub. No.: WO88/05326
PCT Pub. Date: Jul. 28, 1988

[51] Int. Cl.⁴ ............................................. G01N 19/02
[52] U.S. Cl. ............................................................. 73/9
[58] Field of Search ........................................ 73/9, 10

[56] References Cited

U.S. PATENT DOCUMENTS 3,791,489  2/1974  Vernazza et al. ........................ 73/9
3,975,940  8/1976  Brungraber .............................. 73/9
4,798,080  1/1989  Brungraber .............................. 73/9

Primary Examiner—Tom Noland
Assistant Examiner—Michele Simons
Attorney, Agent, or Firm—McAulay Fisher Nissen & Goldberg

[57] ABSTRACT

A device for testing a ski sliding surface comprising a case (1) housing a spiral spring (3) having one end thereof attached to case (1) and the other end to an axle (4) rotatably disposed with respect to case (1), and a support bushing (7) attached to one end of axle (4). The end of the support bushing (7), which is exterior to case (1), holds a disk (8) whose end face (9) intended for interaction with snow or snow imitation surface is made of a material forming the test ski sliding surface. A measuring mechanism for measuring relative rotation of the disk (8) and the case (1) is designed as a ratchet-and-pawl mechanism (10) which has a gear (12) secured on the axle (4) and is provided with a switch (11) for step-by-step engagement of spring-loaded pawls (13, 14) with the gear (12), a scale (18) for sliding capacity measurement disposed on case (1), and a pointer (19) fixed on the other end of axle (4).

14 Claims, 2 Drawing Sheets

DEVICE FOR TESTING SKI SLIDING SURFACE

FIELD OF THE INVENTION

The present invention relates to ski maintenance gear, and more specifically to a device for testing the ski sliding surface.

BACKGROUND OF THE INVENTION

Nowadays in modern skiing success of a skier specializing in cross-country skiing, biathlon, alpine skiing, ski jumping and Nordic combination depends not only on his physical fitness, morale and skill, but also on the proper choice of skis or the type of ski sliding surface made of different materials with or without grooves of different materials with or without grooves of different shape and width, as well as the type of wax applied to the ski sliding surface.

In view of varying snow properties (e.g., due temperature and humidity changes) determining the ski sliding surface friction against the snow, proper selection of the sliding surface type and wax necessitates accurate and timely (on the day of competition) measurements of sliding properties (dynamic friction) and track-holding properties (static friction) of different types of ski sliding surface and ski waxes.

The majority of skiers choose skis and ski wax experimentally by means of multiple testing of a limited number of various ski sliding surfaces and waxes. It is a time-and effort-consuming procedure which, nevertheless, does not yield sufficiently accurate results. That is why when choosing skis, type of their sliding surface and wax sportsmen and coaches rely mostly on personal experience and intuition.

Prior art devices for testing the ski sliding surface smeared with wax or without it due to their structural features do not provide for accurate and timely selection of a desirable type of skis, ski sliding surfaces and waxes.

There is a prior art device for ski wax selection (URSS Inventor's Certificate No. 188340. Int.Cl. A63C 11/04, published in the official bulletin "Otkrytiya, Izobreteniya, Promyshlennye Obraztsy, Tovarnye Znaki", 1966, v. 21) comprising a mock-up ski with ski wax applied to its sliding surface and a percussion mechanism for propelling the mock-up ski on the snow designed as a spring-loaded pusher. The device is intended to determine the sliding properties of different waxes on the basis of measuring the mock-up ski sliding distance when it comes forward.

This device is rather slow in operation as it takes quite a long time to propel the mock-up ski, measure the sliding distance and return the mock-up ski to the initial position. Such a device shows low accuracy of sliding properties measurement due to substantial influence of static friction (with speed approaching zero) and roughness of the snow on which measurements are conducted and also limited functional abilities as the ski wax choice is based only on sliding properties measurement.

A prior art device for testing the ski sliding surface (cf. USSR Inventor's Certificate No. 787051, Int.Cl. A63C 11/04, published in the official bulletin "Otkrytiya, Isobreteniya, Promyshlennye Obraztsy, Tovarnye Znaki", 1980, v. 46) comprises a case housing accommodating a spiral spring one end of which is attached to the case and the other—to an axle, a support bushing an exterior end of which holds a disk whose end face intended for interaction with snow or imitation surface is made of a material forming the test ski sliding surface, and a mechanism for measuring relative rotation of the disk and the case.

The mechanism for measuring relative rotation of the disk and the case contains a limb with a scale and a knob, and also an overrunning clutch for recording the relative rotation value defining snow or imitation surface holding capacity of the test ski sliding surface with ski wax applied to it.

After the device has been set up on the snow the knob of the limb is turned. The spiral spring connected with the limb and the support bushing starts winding up thus giving rise to a growing torque on the support bushing. Winding continues until the torque exceeds the moment of resistance created by the snow-holding force of the test ski sliding surface. The disk together with the support bushing rotates in the same direction with the limb, the starting moment of the rotation being determined by observation, and the knob turning is stopped, while the twist angle value is registered on the scale. The starting moment of the disk rotation is determined owing to the clearance between the limb and the case being jammed by a ball of the overrunning clutch when the relative rotation direction is reversed. On the basis of track-holding capacity measurements taken in the course of testing different disks having their end face smeared with various waxes one chooses the ski wax which is the most suitable under the given conditions.

Said prior art device for testing the ski sliding surface has but limited functional abilities as the described design of the gadget for measuring relative rotation of the disk and the case makes it possible to measure only the track-holding capacity value.

Accuracy of measurements is not high due to the overrunning clutch having a significant dead zone and thus determining the starting moment of the disk rotation with inadequate precision. Rotation of the case by means of the knob attached to it adversely affects the pressure of the device on the snow and causes its displacement that makes the starting moment of the disk rotation too early or too late. The device design does not rule out the possibility of inadvertent measurement errors.

The prior art device is also rather slow-acting and inconvenient in operation, since to take each measurement it is necessary to zeroize the limb scale and to lift the device off the snow for reading out the results as the limb scale is on the case side panel.

Due to the fact that the support bushing of the prior art device has a large diameter and the disk is fixed by means of spring locks, considerable skewing of the disk axis and catching of the spring locks may occur thus increasing disk replacement time.

SUMMARY OF THE INVENTION

The present invention is directed to the provision of a device for testing the ski sliding surface that should make it possible to ensure high accuracy and speed of the sliding capacity measurement. It is also directed at ensuring high accuracy and speed of the track-holding capacity measurement.

The aims of the invention are solved by providing that in a device for testing the ski sliding surface comprising a case accommodating a spiral spring one end of which is attached to the case and the other—to an axle, a support bushing an exterior end of which holds a disk whose face intended for interaction with snow or snow imitation surface is made of a material forming the test ski sliding surface, and a gadget for measuring relative rotation of the disk and the case, according to the invention, the axle is mounted rotatably with one end thereof being furnished with the support bushing, whereas the gadget for measuring relative rotation of the disk and case is designed as a ratchet-and-pawl mechanism which has a gear secured on the axle and is provided with a switch for step-by-step engagement of spring loaded pawls with the gear, a scale for sliding capacity measurement disposed on the case, and a pointer fixed on the other end of the axle.

It is expedient that the device for testing the ski sliding surface contain a stand designed as a base for setting it up on the snow or snow imitation surface, another base with an opening, a ring with a handle mounted in said opening in such a way that it may turn with respect to the opening axis, the case being mounted in the ring for axial movement, the mechanism for measuring relative rotation of the disk and the case containing a scale for measuring track-holding capacity disposed on the case.

It is reasonable that the device for testing the ski sliding surface contain an elastic ring, whereas the inner side surface of the support bushing be furnished with a groove accommodating said elastic ring, the disk being provided with a cylindrical projection having a recess in its face and a groove for holding the disk with the elastic ring in place, and the corresponding end of the axle be provided with a flange disposed in the disk recess.

It is desirable that the case be provided with a holder for mounting a removable ratchet-and-pawl switch control.

It is preferable that the device for testing the ski sliding surface contain a ring rotatably disposed on the case, the mechanism for measuring relative rotation of the disk and the case containing in addition a scale for averaging measurement results disposed on said ring.

The proposed device for testing the ski sliding surface makes it possible to measure two variables that are essential for choosing an appropriate ski wax or ski type, i.e. sliding and track-holding capacity. Measuring these variables does not require any special sites as measurements may be taken right on the track before the start. Measurement of sliding and track-holding capacity is conducted with high accuracy due to introduction of the ratchet-and-pawl mechanism with a switch that provides for accurate determination of the spiral spring twist angle and for the disk stopping. Switch handling by means of the removable control considerably reduces errors involving manual control, whereas introduction of the scale for averaging measurement results makes it possible to prevent random errors of measurement.

The device is easy to handle; it has small-size moving elements permitting to increase the disk rotation speed and consequently to increase response. Introduction of the scale-pointer system and also the arrangement of the scales on the case top simplifies the reading of results.

On the whole, all the advantages cited help to raise the effectiveness of the device operation and bring the test time of 10 types of ski waxes and 20 types of ski paraffins down to 30 minutes.

BRIEF DESCRIPTION OF THE DRAWINGS

The invention will become more fully apparent from the following description of specific embodiments thereof taken in conjunction with the accompanying drawings, wherein.

BEST MODE OF CARRYING OUT THE INVENTION

Figure 1:
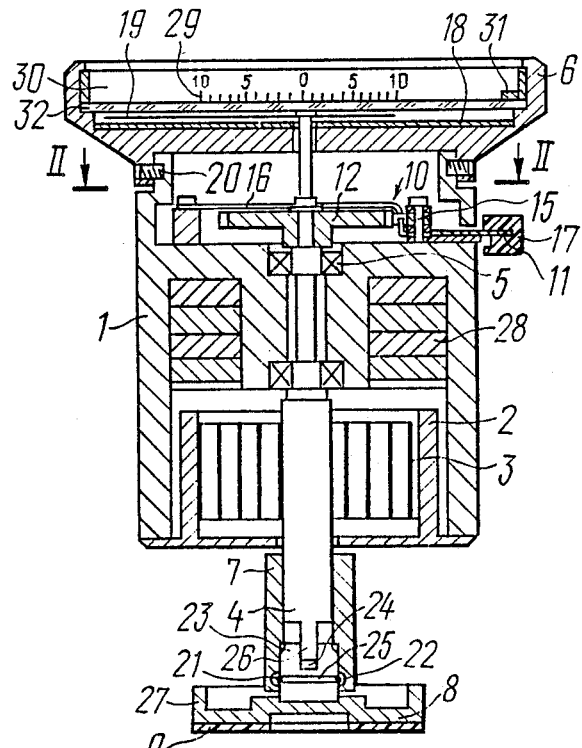
FIG. 1 represents a general view of the device for testing the ski sliding surface (longitudinal section), according to the invention.

The device for testing the ski sliding surface comprises a case 1 (FIG. 1) wherein, in the given embodiment, a socket 2 is made fast and a spiral spring 3 is mounted, one end thereof being attached to the socket 2 and the other end—to an axle 4 arranged rotatably with respect to the case 1 in bearings 5 in alignment with the socket 2. The case 1 has a top 6, and the axle 4 carries a support bushing 7, one end thereof being exterior to the case 1 (in the embodiment under consideration the whole of the support bushing 7 is exterior to the case 1). Said end of the support bushing 7 carries a disk 8 whose face 9 intended for interaction with snow or imitation coating is made of a material forming the test ski sliding surface, e.g. of plastic material, which may be smeared with a ski wax or ski wax combination, ski paraffin or ski paraffin combination. The test ski sliding surface may be also provided with longitudinal grooves of various configurations.

The device contains also a gadget for measuring relative rotation of the disk 8 and the case 1 designed as a ratchet-and-pawl 10 complete with a switch 11. A gear 12 of the ratchet-and-pawl 10 is mounted on the axle 4, the switch 11 provides for step-by-step engagement with the gear 12 of pawls 13 (FIG. 2), 14, mounted on an axle 15 and urged to the gear 12 by a spring 16. In said embodiment the switch 11 (FIG. 1) is designed as a bar member and has two extreme and one mid-position (in FIG. 2 position of the pawls 13, 14 corresponds to the mid-position of the switch 11). For easier handling the switch 11 has a knob 17 (FIGS. 1,2) mounted on the case 1. The gadget for measuring relative rotation of the disk 8 and the case 1 contains also a scale 18 (FIG. 1) for measuring sliding capacity disposed on the top 6 of the case 1, and a pointer 19 mounted on the other end of the axle 4. The top 6 of the case 1 is mounted so that it can rotate with respect to it for aligning "zero" of the scale 18 with the pointer 19 in the absence of a torque produced by the spiral spring 3. Said position of the scale 18 is fixed by means of lock screws 20.

For quick and secure mounting of the disk 8 in the support bushing 7 the device is provided with an elastic ring 21, on the inner side surface of the support bushing 7 there is a groove 22 wherein said ring 21 is disposed, and the disk 8 has a cylindrical projection 23 with a recess 24 in its face and a groove 25 for holding the disk 8 in place by the elastic ring 21. The corresponding end of the axle 4 is provided with a flange 26 disposed in the recess 24 of the disk 8. For convenience in operation the disk 8 is provided with a skirt 27 having notches that prevent its slipping when it is mounted on the support bushing 7 or removed therefrom.

This embodiment provides for changing the unit pressure of the disk 8 on the snow or imitation coating depending on the skier's weight and the sliding surface of his skis. To attain this, a required quantity of replaceable weights 28 are secured inside the case 1.

To obtain average results of measurements the measuring mechanism for measuring relative rotation of the disk 8 and the case 1 is in addition provided with a scale 29 for averaging measurement results graduated in arbitrary units of measurement, placed on an elastic ring 30 with a pointer 31, which is rotatably mounted on the side surface of the top 6. A faceplate 32 mounted in the top 6 over the scale 18 guards the scale 18 and the pointer 19 against damage and soiling.

Figure 2:
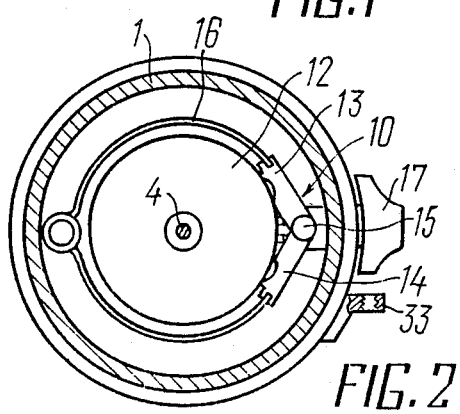
FIG. 2 represents a section taken along the line II—II in FIG. 1.

In case of changes in sliding properties, to control the switch 11 of the ratchet-and-pawl 10 by means of a removable control, e.g. a camera cable release or an automatic release (not shown) the case 1 is provided with a holder 33 (FIG. 2). This prevents the transmission of an "interference" force (such as extra pressure on and movement of the housing) to the device in the course of handling.

Figure 3:
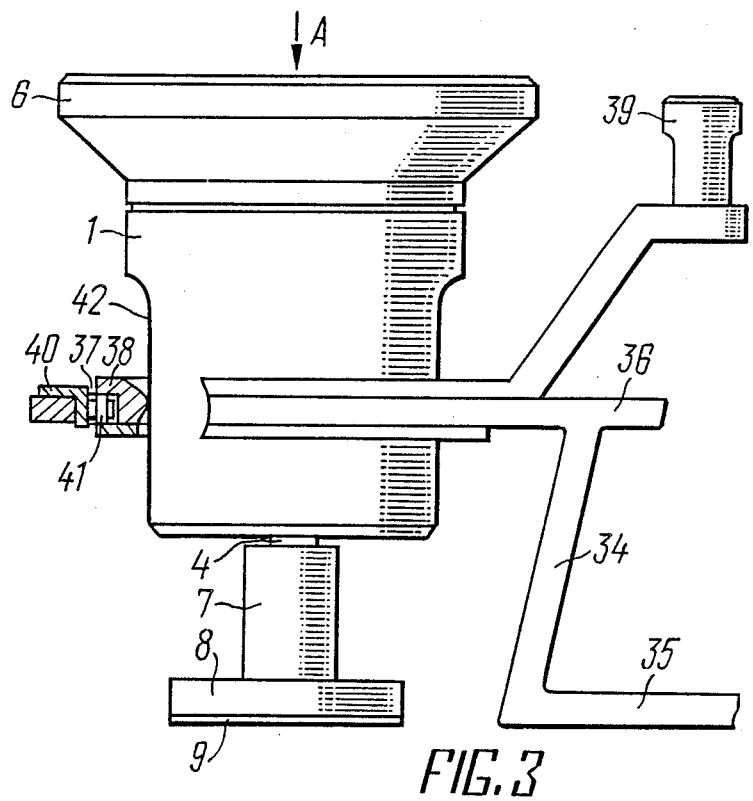
FIG. 3 represents a general view of the device for testing the ski sliding surface with a stand (partial cutaway view of the stand), according to the invention.

To measure track-holding capacity, the device for testing the ski sliding surface contains a stand 34 (FIG. 3) designed as a base 35 for setting it up on the snow or imitation coating, another base 36 with an opening 37, a ring 38 with a handle 39 mounted in said opening 37 by means of an arm 40 in bearings 41 in such a way that it may turn with respect to the axis of the opening 37. The case 1 is provided with bevels 42 preventing the case 1 from turning in relation to the ring 38 and ensuring a possibility of its axial displacement.

Figure 4:
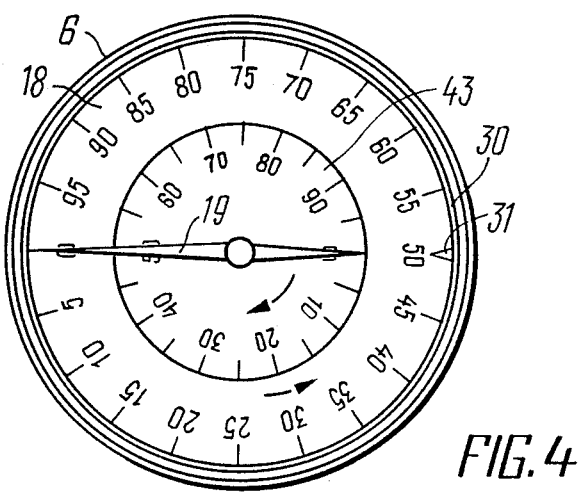
FIG. 4 is a view looking in the direction of arrow A in FIG. 3, according to the invention.

The mechanism for measuring relative rotation of the disk 8 and the case 1 contains a scale 43 (FIG. 4) for measuring track-holding capacity disposed on the top 6 of the case 1 concentrically with the scale 18 for measuring sliding capacity. For easier reading of the sliding and track-holding values of the "O" mark of the scale 18 is displaced from the "O" mark of the scale 43 by 180°, and for more accurate reading of sliding values of the scale 18 is disposed along the perimeter of a larger circle the smaller end of the pointer 19 being used for measuring track-holding capacity.

Each scale 18, 43 is calibrated in arbitrary units of measurement and has 100 divisions. The number of divisions is chosen for the sake obtaining accuracy of measurements and easier handling of the device and one does not need to know the scale division value because what matters is the comparison of sliding and track-holding capacity for test ski sliding surfaces.

The proposed device makes it possible to test the ski sliding capacity in two modes: a mode of dynamic friction (sliding) and a mode of static friction (track-holding).

Before starting measurements the device is brought to initial position by means of putting the disk 8, e.g. with its face smeared with lubricant, on the support bushing 7 (FIG. 1). The disk 8 is fitted into the support bushing 7 by means of the cylindrical projection 23 and by rotation about the axle 4 the recess 24 of the cylindrical projection 23 is brought into alignment with the flange 26 of the axle 4. The possibility of free rotation of the disk 8 about the axle 4 is thus precluded. Then the cylindrical projection 23 of the disk 8 is moved into the support bushing 7 until the elastic ring 21 registers with the groove 22 thus providing for the disk 8 being held in the support bushing 7.

To measure sliding capacity the switch 11 by means of the knob 17 is moved clockwise into extreme position (position 1), said switch 11 disengaging the pawl 13 (FIG. 2) from the gear 12 and throwing the latter into engagement with the pawl 14 which is urged to the gear 12 by the spring 16. This position of the switch 11 enables the spiral spring 3 (FIG. 1) to wind-up. By rotating the disk 8 clockwise in relation to the case 1 the spiral spring 3 is wound to a certain angle, e.g. of 360°, which corresponds to 100 divisions of the scale 18 (FIG. 4) to measure sliding capacity. The ratchet-and-pawl 10 (FIG. 1) holds the pointer 19, disk 8 and spiral spring 3 in set position. Then the device is set up on the snow or imitation surface with the face 9 of the disk 8 and the switch 11 is moved counterclockwise into extreme position (position 11) wherein the switch 11 disengages the pawl 14 (FIG. 2) from the gear 12 and throws the latter into engagement with the pawl 13. The axle 4 (FIG. 1) with the disk 8 and the pointer 19 starts spinning up under the action of the torque created by the spiral spring 3 and the moment produced by sliding friction force between the face 9 of the disk 8 (and, consequently, the test sliding surface of the skis) and the snow. When direction of the angular velocity of the axle 4 changes, it is brought to a stop along with the disk 8, the pointer 19 stopping at a specific division of the scale 18 (FIG. 4) for measuring sliding capacity, e.g. at the division '60' which corresponds to the sliding capacity of 60 arbitrary units. Indications are read and entered in a table or registered by placing the pointer 31 opposite the longer arm of the pointer 19. The spring-loaded pawl 13 prevents the rotation of the axle 4 with the disk 8 (FIG. 2) in the opposite direction. The use of the ratchet-and-pawl 10 (FIG. 1) provides for high accuracy determination of the rotation stopping moment of the axle 4 and the disk 8 and also for winding the spiral spring 3 to a specific angle in order to release the energy of said spring 3 later for rotating the disk 8.

To improve the measurement accuracy a test with one and the same disk 8 may be repeated several times with avaraging the measurement results. The second result of the measurement is also read and entered in a table and by means of the scale 29 for averaging measurement results this result may be summed with the previous result and after that a mean result may be obtained. To do this the pointer 31 (FIG. 4) is shifted to the longer arm of the pointer 19 by ½ of the indication value of the scale 29 (FIG. 1). After the third, fourth, etc. measurement the pointer 31 is shifted in the direction described above by ⅓, ¼, etc. of the indication value of the scale 29. The pointer 31 always registers the average result of all measurements taken.

In case it is necessary to improve the sliding capacity measurement accuracy the switch 11 (FIG. 1,2) is moved to extreme position (position 11) by some removable control means fixed in the holder 33 (FIG. 2) and precluding a possibility of transmission of the "interference" force of the hand of the operator causing additional pressure on the device or its displacement from the testing site.

The use of the removable control of the switch 11 (FIG. 1) makes it possible to reduce the number of measurements to be taken and, consequently, to raise the effectiveness which is increased also by the introduction of the scale 18-pointer 19 system, arrangement thereof on the top 6 of the case 1 being very convenient for reading measurement results.

The sliding capacity measurement results serve as a basis for selecting the most suitable for specific conditions type of the sliding surface with the ski wax (paraffin) applied to it or without it. In events like ski jumping, alpine skiing and cross-country skiing (when only skating stride is used) to achieve success in a competition it is sufficient to determine only one parameter, i.e. the sliding capacity, whereas in other events like Nordic combination, biathlon, or cross-country skiing besides the sliding capacity it is necessary to know also the other parameter—the track-holding capacity.

Measurements of the track-holding capacity are conducted after the case 1 has been mounted in the ring 38 (FIG. 3) in such a way that the end surface 9 of the disk 8 smeared with ski wax should be able to contact with the snow or with some snow imitation surface. The switch 11 (FIG. 1) is moved to the extreme position '1' and then by turning the handle 39 (FIG. 3) the ring 38 with the case 1 mounted therein is rotated counter-clockwise causing the spiral spring 3 (FIG. 3) to wind up and producing a torque on the disk 8, which increases in proportion to the twist angle. The scale 43 (FIG. 4) for measuring track-holding capacity rotates concurrently with the case 1 and the pointer 19 connected to the disk 8 (FIG. 1) stays fixed. One proceeds with turning the handle 39 (FIG. 3) and, consequently, with winding of the spring 3 (FIG. 1) until the pointer 19 starts turning. It means that the torque produced by the spiral spring 3 has exceeded the anti-torque moment produced by the track-holding force between the face 9 of the disk 8 and the snow or imitation surface. At the starting moment of rotation of the pointer 19 and after one has ceased turning the handle 39 (FIG. 3) the pointer 19 (FIG. 4) is fixed with respect to a certain division of the scale 43 for measuring track-holding capacity, pointed to by the smaller arm of the pointer 19. The spring-loaded pawl 14 (FIG. 2) in engagement with the gear 12 prevents rotation of the axle 4 (FIG. 1) with the disk 8 in the opposite direction under the influence of the wound-up spring 3.

Indications are read and entered in a table or "memorized" by means of the pointer 31 (FIG. 1). Measurements may be repeated several times with their results being averaged as it has been previously described.

After tests with one disk 8 (with one type of lubricant) one passes to tests with another disk 8 (another type of lubricant).

The device provides for varying the unit pressure depending on the skier's weight and the sliding surface of his skis. This can be obtained by removing or adding the weights 28.

It should be noted that the sliding capacity measurement may be also conducted when the case 1 is mounted on the stand 34 (FIG. 3) in the way described above and to obtain higher accuracy of the track-holding capacity measurements it is expedient to use a removable control means of the switch 11 (FIG. 1) as it has been described above.

Thus, the proposed device for testing the ski sliding surface makes it possible to conduct quick and accurate determination of sliding and track-holding variables, knowledge thereof being important for selecting a ski wax or a type of skis which are the best for given conditions.

INDUSTRIAL APPLICABILITY

The invention can find application in modern skiing sports (such as ski jumping, alpine skiing, biathlon, Nordic combination or cross-country skiing) for determining sliding and track-holding capacity of the ski sliding surface, including instances when the ski sliding surface is smeared with special lubricants or treated mechanically.

We claim:
1. A device for testing the ski sliding surface, comprising:
   a case housing accommodating a spiral spring having one end thereof attached to the case and the other end attached to an axle;
   a support bushing, an exterior one end of said bushing holding a disk whose end face is intended for interaction with a snow or snow imitation surface and is made of a material forming a ski test sliding surface;
   measuring surface means for measuring relative rotation of the disk and the case; and wherein
   the axle (4) is rotatably mounted at one end thereof and a support bushing (7) for supportedly mounting said other end;
   said measuring means for measuring relative rotation of the disk (8) and said case (1) includes a ratchet-and-pawl mechanism (10) and a gear (12) secured on said axle (4);
   a switch (11) for step-by-step engagement of spring-loaded pawls (13, 14) with the gear (12);
   a scale (18) for sliding capacity measurement disposed on the case (1); and
   a pointer (19) fixed on the other end of the axle (4).
2. A device for testing the ski sliding surface as claimed in claim 1, including:
   a stand (34) in the form of a first base (35) for setting it up on the snow or snow imitation surface;
   a second base (36) having an opening (37);
   a ring (38) and a handle (39) mounted in said opening (37) for rotation relative to the axis of the opening (37), said case (1) being mounted in the ring (38) for axial movement; and
   said measuring means for measuring relative rotation of the disk (8) and the case (1) including a scale (43) for measuring track-holding capacity disposed on the case (1).
3. A device for testing the ski sliding surface as claimed in claim 2, including:
   an elastic ring (21), the inner side surface of the support bushing (7) having a groove (20) accommodating said elastic ring (21), the disk (8) being provided with a cylindrical projection (23) having a recess (24) in its end face; and
   a groove portion (25) and a plastic ring (21) for holding the disk (8); and
   the corresponding end of the axle (4) being provided with a flange (26) disposed in the recess (24) of the disk (8).
4. A device for testing the ski sliding surface as claimed in claim 3, comprising:
   a ring (30) rotatably disposed on the case (1); and
   said measuring means for measuring relative rotation of the disk (8) and said case (1) contains measurement results averaging scale (29) disposed on said ring (30).
5. A device for testing the ski sliding surface as claimed in claim 2, wherein said case (1) is provided with a holder (33) for mounting a removable control means of the switch (11) of the ratchet-and-pawl mechanism (10).
6. A device for testing the ski sliding surface as claimed in claim 5, comprising:
   a ring (30) rotatably disposed on the case (1); and
   said measuring means for measuring relative rotation of the disk (8) and said case (1) contains measure- ment results averaging scale (29) disposed on said ring (30).

7. A device for testing the ski sliding surface as claimed in claim 2, comprising:
   a ring (30) rotatably disposed on the case (1); and
   said measuring means for measuring relative rotation of the disk (8) and said case (1) contains measurement results averaging scale (29) disposed on said ring (30).

8. A device for testing the ski sliding surface as claimed in claim 1, including:
   an elastic ring (21), the inner side surface of the support bushing (7) having a groove (20) accommodating said elastic ring (21), the disk (8) being provided with a cylindrical projection (23) having a recess (24) in its end face; and
   a groove portion (25) and a plastic ring (21) for holding the disk (8); and
   the corresponding end of the axle (4) being provided with a flange (26) disposed in the recess (24) of the disk (8).

9. A device for testing the ski sliding surface as claimed in claim 8, wherein said case (1) is provided with a holder (33) for mounting a removable control means of the switch (11) of the ratchet-and-pawl mechanism (10).

10. A device for testing the ski sliding surface as claimed in claim 9, comprising:
    a ring (30) rotatably disposed on the case (1); and
    said measuring means for measuring relative rotation of the disk (8) and said case (1) contains measurement results averaging scale (29) disposed on said ring (30).

11. A device for testing the ski sliding surface as claimed in claim 8, comprising:
    a ring (30) rotatably disposed on the case (1); and
    said measuring means for measuring relative rotation of the disk (8) and said case (1) contains measurement results averaging scale (29) disposed on said ring (30).

12. A device for testing the ski sliding surface as claimed in claim 1, wherein said case (1) is provided with a holder (33) for mounting a removable control means of the switch (11) of the ratchet-and-pawl mechanism (10).

13. A device for testing the ski sliding surface as claimed in claim 12, comprising:
    a ring (30) rotatably disposed on the case (1); and
    said measuring means for measuring relative rotation of the disk (8) and said case (1) contains measurement results averaging scale (29) disposed on said ring (30).

14. A device for testing the ski sliding surface as claimed in claim 1, comprising:
    a ring (30) rotatably disposed on the case (1); and
    said measuring means for measuring relative rotation of the disk (8) and said case (1) contains measurement results averaging scale (29) disposed on said ring (30).

* * * * *